(12) United States Patent
Aletta

(10) Patent No.: US 6,699,673 B2
(45) Date of Patent: Mar. 2, 2004

(54) PROTEIN METHYLARGININE-SPECIFIC ANTIBODIES

(75) Inventor: John M. Aletta, Williamsville, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 64 days.

(21) Appl. No.: 09/745,904

(22) Filed: Dec. 21, 2000

(65) Prior Publication Data

US 2002/0052014 A1 May 2, 2002

Related U.S. Application Data

(60) Provisional application No. 60/171,812, filed on Dec. 22, 1999.
(51) Int. Cl.$^7$ .............................................. G01N 33/53
(52) U.S. Cl. .................... 435/7.1; 435/7.92; 424/184.1; 424/185.1; 436/506; 436/518; 514/2; 530/304
(58) Field of Search ........................... 424/184.1, 185.1; 436/506, 518; 514/12; 530/324; 435/7.1, 7.92

(56) References Cited

FOREIGN PATENT DOCUMENTS

WO        9911667        3/1996

OTHER PUBLICATIONS

Siebel, et al, The Essential Yeast RNA Binding Protein Np 13p is Methylated, Proceedings of the National Academy of Sciences, USA, Nov. 1996, vol. 93, pp. 13641–13646.

Brahms, et al, The C–Terminal RG Dipeptide Repeats of the Spliceosomal Sm Proteins D1 and D3 Contain Symmetrical Dimethylarginines, Which Form a Major B–Cell Epitope for Anti–Sm Autoantibodies, The Journal of Biological Chemistry, Jun, 2, 2000, vol. 275, No. 22, pp. 17122–17129.

*Primary Examiner*—Long V. Le
*Assistant Examiner*—Changhwa J Cheu
(74) *Attorney, Agent, or Firm*—Hodgson Russ LLP

(57) ABSTRACT

The present invention provides antisera that specifically recognize peptides containing methylated arginines. The present invention also provides peptides for producing the antisera. Also provided is a method for the detection of methylation status of proteins and peptides, and compositions that affect the methylation status.

9 Claims, 4 Drawing Sheets

US 6,699,673 B2

PROTEIN METHYLARGININE-SPECIFIC ANTIBODIES

This application claims priority to U.S. provisional patent applications Ser. No. 60/171,812 filed on Dec. 22, 1999, the disclosure of which is incorporated herein by reference.

FIELD OF THE INVENTION

This invention relates to the field of protein methylation. More particularly, the present invention relates to antibodies that specifically recognizes peptides and proteins containing methylated arginines.

BACKGROUND OF THE INVENTION

Protein methylation is considered to play an important role in cellular functions such as signaling. In eukaryotic cells, proteins are methylated on carboxyl groups or on the side chain nitrogen of the amino acids lysine, arginine or histidine.

N-methylation, such as that occurring on arginine residues in proteins, has generally been regarded as a constitutive and irreversible post-translational modification. However, there may be exceptions to this view. For example, NGF has been reported to dramatically alter the pattern of protein methylation observed in PC12 cells after metabolic radiolabeling of protein in intact cells, and by in vitro labeling of proteins in cell extracts.

The enzymes responsible for protein methylation, protein arginine methyl transferases (PRMT) are currently classified into two distinct categories. One type of activity (Type I) produces asymmetric dimethylation of the $n_1$ terminal guanidino nitrogen of arginines in substrate proteins, particularly glycine- and arginine-rich (GAR) segments of proteins. Proteins that are substrates for this reaction include nucleolin, fibrillarin, and several hnRNPs. Type II arginine methyltransferase activity produces symmetric dimethylation of both terminal nitrogens of specific protein arginines. Myelin basic protein is a recognized substrate for this activity.

While protein methylation is recognized to be important in cell signaling mechanisms, its precise role in neuronal growth and differentiation remains to be elucidated. Biochemical analysis of cellular protein methylation is currently hindered by the lack of a simple means of determining the methylation status of native cellular proteins. Mass spectroscopy, though precise, is a very specialized and time-consuming technique. Metabolic radiolabeling of methyl-proteins is problematic owing to the vicissitudes of a variety of kinetic parameters related to cellular enzymes and protein substrates. Thus, there is an ongoing need to develop tools that will enable detection of methylarginine proteins, detection of their methylation status and detections of compositions that affect methylation.

SUMMARY OF THE INVENTION

The present invention provides antibodies to arginine methylated proteins. By using these antibodies, the methylation status of cellular proteins involved in cell metabolism and function can be characterized.

The present invention also provides a method of producing antibodies that discriminates between arginine methylated and non-arginine-methylated proteins or peptides. These antibodies are prepared by using peptides containing one or more methylated arginines. The antibodies are reactive against the methylated form of the peptides.

The present invention also provides a method for detecting the presence of methylated proteins in a sample. The method comprises the steps of contacting the sample with antibodies of the present invention and detecting the proteins or peptides bound to the antibody. The method can also be used for identification of compositions that affect methylation of proteins.

DETAILED DESCRIPTION OF THE INVENTION

Figure 1:
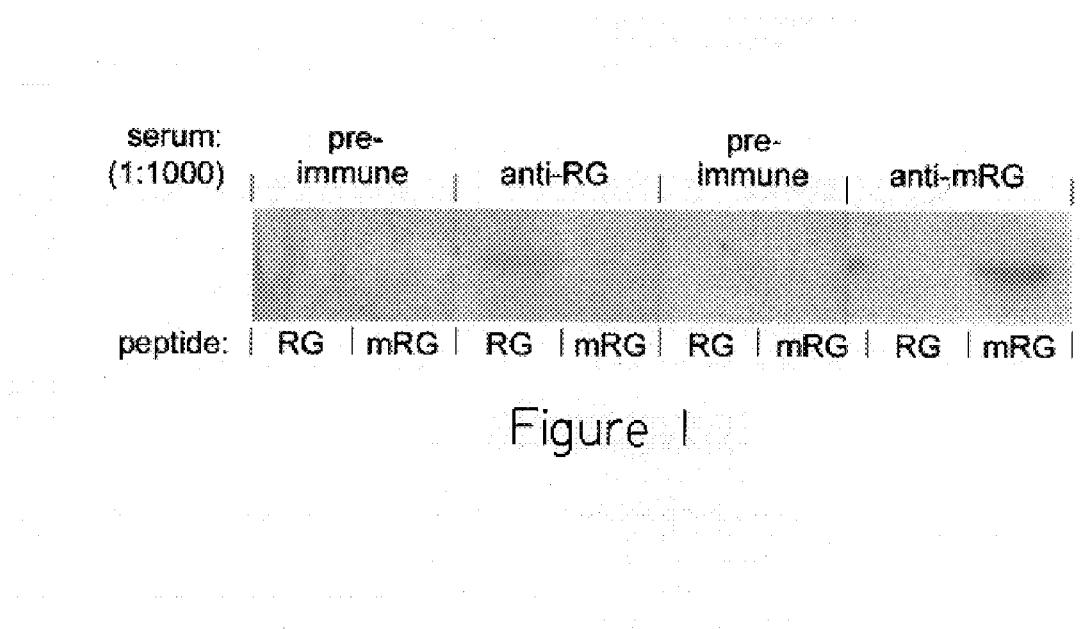
FIG. 1 is a representation of a western blot of methylated (mRG) and non-methylated (RG) peptides using the antisera according to the present invention. Anti-RG is the antisera generated against the unmethylated peptide and anti-mRG is the antisera generated against the methylated peptide.

The present invention provides peptides for generation of methylation-specific antibodies. The antibodies specifically recognizes methylated proteins, particularly, methylarginine proteins. The antibodies of the present invention may be used to determine the methylation status of proteins and to identify compositions that can affect the methylation status of proteins.

Any methylated-arginine containing peptide may be used to generate antisera according to the present invention. In a preferred embodiment, peptides rich in arginine and glycine are used to generate antibodies. As those skilled in the art will appreciate, an antigenic site generally consists of about 5–20 amino acids. Thus, peptides containing at least 5 amino acids can be used as immunogens. In a preferred embodiment, the peptides contain between 7 and 20 amino acids. The peptides should contain at least one arginine in the methylated form. In a preferred embodiment, the peptide contains one or more glycine-arginine-glycine (GRG) motifs, with the arginine in the GRG motif being methylated. These peptides can be synthesized by standard methods of peptide synthesis well known to those skilled in the art. An automated peptide synthesizer can be programmed to concentrate glycine and methylarginine in an alternating fashion by amide bond formation. The choice of mono-or demethyl-arginine in either the symmetric or asymmetric configuration can be chosen based upon the epitope desired for recognition and then loaded into the proper reaction vessels in the synthesizer.

The antibodies of the present invention specifically recognize peptides or proteins containing methylated arginines. Those skilled in the art will recognize that while many arginine methylation sites are found in glycine rich areas, other amino acids may also be present in the vicinity of arginines that undergo methylation. Thus the epitopes that are recognized by the antibodies of the present invention have at least one arginine that can undergo methylation. The antibody will bind to the epitope only when the arginine is methylated.

The antibody according to the present invention may be polyclonal or monoclonal, or an antigenic binding fragment thereof. An antibody composition useful in the present invention is an anti-peptide antibody characterized as containing antibody molecules that specifically immunoreact with a methylated form of a protein or peptide. The methylated proteins contempleted in the present invention are proteins that have methylated arginines. There may be a single methyl group on the terminal guanidino nitrogen of an arginine or two methyl groups. When there are two groups present, these groups may be present in either a symmetrical or asymmetrical configuration.

Antibodies may be produced using procedures well known to those skilled in the art. For example such methodologies are described by Harlow and Lane in Antibodies: A Laboratory Manual, Cold Springer Harbor Laboratory, Cold Spring Harbor, 1998, pp 1–725. Suitable hosts for producing antibodies include mice, rats, rabbits, cows, sheep, goats and humans. Generally, for polyclonal antibodies, the host is immunized by administering the antigen, either alone or in the form of a protein conjugate. To use as a protein conjugate, a cysteine may be attached at the C-terminus of the peptide to permit attachment to an immunogenic protein through a connecting bridge, such as maleimidobenzoylated keyhole limpet hemocyanin (KLH). Other immunogenic proteins include albumin and the like.

The peptide or immunconjugate is administered to the host by a suitable method such as by injection, either intraperitoneally, intravenously, subcutaneously, or by intrafoot pad. The immungenic composition may include an adjuvant. The immunization protocol includes an initial injection and may be followed by several booster injections at several weeks interval. To detect if the host is producing the desired antibodies, the serum or plasma of the host can be tested against methylated and non-methylated peptides. Hosts having positive reaction can be then used for generating a supply of the antibodies.

Antibodies of the present invention also include monoclonal antibodies. The method involves injecting an animal with an immunogen. The animal is sacrificed and cells taken from the spleen, which are then fused with myeloma cells. The resulting hybridoma cells are then screened for the production of the desired antibodies. The lymphocytes can also be exposed to the antigen in vitro.

Antigenic binding fragments of antibodies include Fab and $F(ab)'_2$. Digestion of antibodies to produce antigenic binding fragments can be accomplished by routine techniques. For example, Fab fragments can be produced by using papain and $F(ab)'_2$ can be produced by treatment with pepsin.

The antibodies of the present invention can be used for identification of proteins or peptides that undergo methylation, and for determining the methylation status of proteins or peptides, by immunological techniques such as western blots or immunoassays. The present antibodies can also be used for identification of compositions that effect or affect methylation. Accordingly, the present invention can be used for detection of methyltransferases and demthylases.

The following examples are presented to further illustrate the various embodiments but are not meant to be restrictive.

EXAMPLE 1

This embodiment describes the systhesis of a peptide that can be used to elicit antibodies that are specific for arginine methylated proteins or peptides. In one illustration of this embodiment, a peptide amide ($H-CGRGRGRGRGRGRG-NH_2$ where R indicates $N^\omega,N^\omega$-dimethylarginine) was synthesized by solid phase method using fluoren-9-yl-methylozycarbonyl (Fmoc) chemistry. All arginine residues used in the synthesis were modified by asymmetric dimethylation of the terminal guanidino group. Automated chain assembly, 0.1 mmol scale, was carried out in dimethylformamide (DMF) on a continuous-flow peptide synthesizer (Millipore model 9050) using Sieber amide resin (0.16 mmol $NH_2$-groups per one gram resin). The side chain protecting group for dimethylarginine was Mts. Fmoc removal was accomplished with 25% piperidine in DMF. Single couplings were carried out for 1.5 h using in situ Fmoc-acid/N-[(10H-benzotiazol-1-yl) (dimethylamine) methylene]-N-methylmethanamunium tetrafluoroborate N-oxide (TBTU)/1-hydroxybenzotriazole (HOBt)/N-diisopropylethylamine (DIEA) in the proportions of 1/0.9/1/1.8 (0.4 mmol Fmoc-amino acid,=4 equivalents). Following chain assembly, the side-chain protected peptide resins were washed with dichloro-methane (DCM) and petroleum ether (fraction 40–60° C.) and dried in vacuo for 24 h.

Cleavage/deprotection cocktails (20 ml/g peptide resin) containing trifluoroacetic acid (TFA)/$H_2O$/tiisoproplysilane (TIPS) (proportions of 95/2.5/2.5) were prepared fresh prior to use. The peptide resins were swollen in DCM, filtered and cleavage cocktail was added and capped under $N_2$. The time for cleavage/deprotection (1 to 5 h) was established according to real time reverse phase high performance liquid chromatography (RP HPLC) separation of reaction mixture. The peptide mixture was filtered separately from the resins, washed 2× with 2 ml trifluoroacetic acid (TFA) and evaporated in vacuo at room temperature. The peptide was precipitated with 20 volumes cold ethyl ether, the pellet were separated, washed with ether (3×30 ml) and dried. The peptide was additionally deprotected for 45 min with trimethylsilyl bromide (TMS-Br)/thioanisol according to a modified procedure of Sparrow and Monera (1996, Peptide Res., 9(5):218–22).

Peptides were purified by preparative RP HPLC on Waters RCM 15RP18 column (100×25 mm I.D.) using a linear gradient of acetonitrile (0–35% in 70 min) in the presence of 0.1% TFA and stored as lyophilized powder. The purity and identity of the peptide was confirmed by RP HPLC and electrospray ionization mass spectroscopy (ESI MS).

EXAMPLE 2

In this embodiment, an antiserum specific for methylated arginine residues, was generated. To illustrate this embodiment, two 16 mer peptides were synthesized. The first peptide had the sequence CGRGRGRGRGRGRGRG (SEQ ID NO:1; Peptide 1), whereas the second peptide had the same sequence except that all the arginines are methylted, represented as CGmRGmRGmRGmRGmRGmRGmRG (Peptide 2). The first peptide contains non-methylated arginine (R) residues, and the second peptide contains asymmetric dimethylarginine (mR) at each corresponding arginine site. The amino acid glycine was chosen in alternating positions to maximize the antigenic presentation of the asymmetrically methylated terminal nitrogen of the mRG peptide. Thus, the RG peptide (Peptide 1) serves as a control peptide for antigenic responses directed against the configuration of arginine and glycine amino acids in contradistinction to the desired asymmetric dimethyl-epitope of the mRG peptide. The N-terminal cysteine allows coupling of the hapten to keyhole limpet hemocyanin (KLH) via a stable thioether linkage to increase the overall antigenicity of the peptides.

Each of the above peptides was dissolved in deionized water (10 µg/µl) and 200 µl was removed for reaction with 1 mg/ml KLH and the sulfhydryl cross-linking agent, sulfosuccinimidyl 4-[N-maleimidomethyl]-cyclohexane-1-carboxylate (SMCC). This mixture, containing 100 µg of peptide, was injected subcutaneously into rabbits. Following the first immunizing injection, the same procedure was repeated for booster injections after 2, 4, 6, 8, 10, 14 and 18 weeks. After the fifth week, a test bleed was performed. Larger volume bleeds were performed at the 7th, 11th, 15th and 19th weeks.

The above antisera can be affinity purified to reduce non-specific interactions. A column of sepharose beads can be cross linked with mRG peptide (Peptide 2) by techniques well known to those skilled in the art. Such a column can be used to separate the antibodies to methyl-specific epitopes from other components of ammonium sulfate treated crude serum. After elution of these antibodies from the first column with glycine, the antibodies can be applied to a second column cross-linked with the immobilized, non-methylated RG peptide (Peptide 1). The eluent from the second column will contain an enriched fraction of antibodies directed against dimethylarginine epitopes.

EXAMPLE 3

In this embodiment, the antisera from Example 2 was used to discriminate between methylated and non-methylated arginine containing peptides. An enzyme immunoassay was carried out using standard immunoassay techniques well known in the art. Briefly, RG (Peptide 1) or mRG peptide (Peptide 2) was coated on to microtitre plates and various antiserum dilutions were added. After removal of unbound materials, anti-IgG conjugated to horse radish peroxidase was added. After appropriate incubation, a peroxidase substrate was added and color development was recorded in a spectrophotometer. The results of an enzyme immunoassay of antiserum obtained from the 2nd bleeding of immunized rabbits are presented in Table 1. A titre that produced a net absorbance of 1.0 was used as a comparison point.

TABLE 1

|  | Titre versus | |
| --- | --- | --- |
| Rabbit sera | RG | mRG |
| anti-RG peptide | 1/155,000 | 1/24,000 |
| anti-mRG peptide | 1/25,000 | 1/350,00 |

These results indicate that the anti-RG peptide sera shows specificity against the non-methylated form of the peptide, and the anti-mRG peptide sera shows specificity against the methylated form of the peptide.

To further confirm the specificity of the antisera from Example 2, western blotting was carried out using the peptides used to raise the antisera. Briefly, approximately, 100 ng each of Peptide 1 and Peptide 2 were immobilized on a western blot membrane for reaction with antisera. Western blotting was performed by techniques standard and well known to those skilled in the art. The results are shown in FIG. 1. RG represents the non-methylated form of the peptide and mRG is the methylated form. Preimmune sera were taken from all animals prior to immunization with the peptides. As shown in FIG. 1, preimmune sera do not recognize either form of the peptide. Anti-RG recognizes only the unmodified RG peptide. The antiserum raised against the methylated form of the RG peptide (mRG) similarly, recognizes only the methylated form of the peptide.

These results indicate that the antiserum raised according to the present invention is specific for methylated-arginine containing peptides and is able to discriminate between the methylated and non-methylated peptides.

EXAMPLE 4

Figure 2:
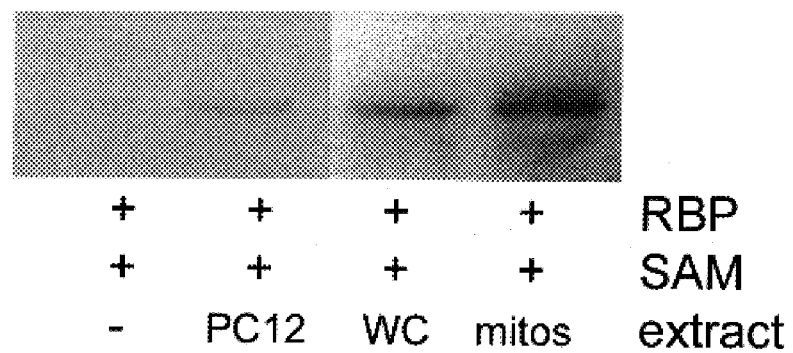
FIG. 2 is a representation of in vitro methylation of recombinant MBP-RBP16 as detected by antisera against methylated peptides. In vitro methylation was accomplished by incubation with S-methyladenosine (SAM), and PC12 cell extract (PC12), whole cell extract of T. brucei (WC) or mitochondrial extract of T. brucei (mitos).

In this embodiment, the antisera of the present invention was used to determine methylation status of proteins in vitro. To illustrate this embodiment, the RNA binding protein from *T. brucei* (RBP16) was expressed as a fusion with maltose binding protein (MBP-RBP16). The fusion protein has a mass of 55 kDa. The recombinant protein from *T. brucei* contains 5 GRG repeats. The ability of the antisera of the present invention to detect methylated form of this protein was determined by using crude cell extracts as a source of the enzyme protein arginine methyltransferase. To achieve methylation, 1 µg of MBP-RBP16 was incubated in Tris buffer (pH 8.0) containing 100 µM S-adenosylmethionine (SAM) and no extract (−), 10 µg of a PC12 cell nuclear extract (PC12), 100 μg of a whole cell extract of *T. brucei* (WC) or 50 μg of a *T. brucei* mitochondrial extract (mitos). The reaction tube contents were separated on a 10% SDS PAGE gel and transferred to PVDF membrane. The membrane was incubated with 1:1000 dilution of the anti-mRG serum and $^{125}$I-labeled anti-rabbit secondary antibody was used to detect the binding of the primary anti-mRG antiserum by autoradiography. As shown in FIG. 2, no detectable signal is observed in the lane without any extract. A 2.5 fold increased signal is observed in the lane containing PC12 extract while *T. brucei* WC and mitos extracts increased the signal by 10.6 and 17.9 fold respectively. These results demonstrate that the antibodies of the present invention can be used to identify methylation of proteins in vitro.

EXAMPLE 5

Figure 3:
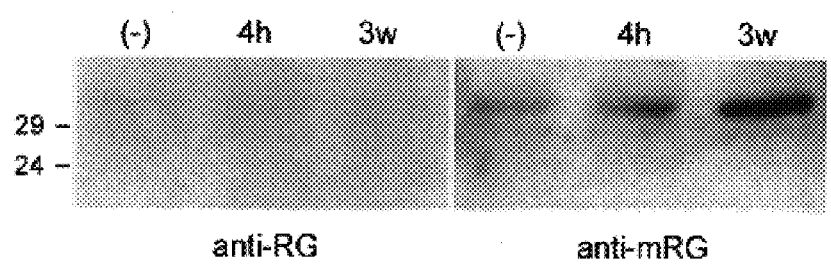
FIG. 3 is a representation of the differential recognition of PC12 cell proteins by anti-RG and anti-mRG antibodies. Proteins were extracted from cells grown in the absence of NGF (−) or in the presence of NGF at 4 hours (4 h) or 3 weeks (3 W) and transferred to a western blot for detection by the two antisera.

This embodiment demonstrates the use of the antisera of the present invention to detect proteins that undergo arginine methylation. To illustrate this embodiment, the effect of NGF, which is known to induce neurite growth and differentiation of PC12 cells on PC12 cell proteins was investigated. PC12 cells were cultured without NGF (−) and with NGF (song/ml) for 4 hours (4 h) or with NGF for 3 weeks (3 W). Soluble cell proteins were collected by hypotonic cell lysis followed by centrifugation at 12,000× g. Equal protein was loaded in each lane of a 10% SDS-PAGE gel. Separated proteins were transferred to a PVDF membrane and probed with a 1:1000 dilution of anti-RG and anti-mRG. As shown in FIG. 3, the pattern of immunoreactive proteins recognized by anti-mRG is quite different from that observed when using antisera generated against the control RG peptide (Peptide 1). The anti-mRG lanes exhibit a strong signal at Mr ~30 kDa, which increases after NGF treatment. The control antisera (against Peptide 1) shows a faint signal at the same point, which is not affected by treatment with NGF. This demonstrates the utility of antisera against methylarginine peptides to identify targets of arginine methylation.

EXAMPLE 6

Figure 4:
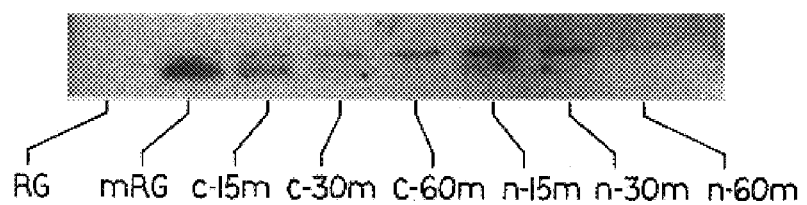
FIG. 4 is a representation of the detection of the activity of protein N-demethylase using the anti-mRG antibodies of the present invention for lanes containing the non-methylated peptide (RG); methylarginine peptide (mRG); mRG plus PC12 cell cytosolic extract for 15 minutes (c-15), 30 minutes (c-30 m), or 60 minutes (c-60); or mRG plus PC12 cell nuclear extract for 15 minutes (n-15 m), 30 minutes (n-30 m) or 60 minutes (n-60 m).

This embodiment demonstrates the use of the antibodies of the present invention to identify cellular compositions that affect the methylation status of proteins. To illustrate this embodiment, cell extracts were prepared and incubated for a desired period of time. The action of N-demethylase is expected to cause a reduction in the methylation status of proteins. The cells extracts were electrophoresed on a 12% SDS PAGE and the Western blots (on PVDF membrane) were incubated with the antibody to the methyarginine peptide. FIG. 4 shows the results for lanes containing the non-methylated peptide (RG); methylarginine peptide (mRG); mRG plus PC12 cell cytosolic extract for 15 minutes (c-15), 30 minutes (c-30 m), or 60 minutes (c-60); or mRG plus PC12 cell nuclear extract for 15 minutes (n-15 m), 30 minutes (n-30 m) or 60 minutes (n-60 m). Thus, there is seen a shift in the mobility of the reactive peptide band and a decrease in the reactivity with increasing incubation times. These results demonstrate that the antibodies of the present invention can be used for detecting the activity of, and the subcellular localization of N-demethylases.

From the foregoing, it will be obvious to those skilled in the art that various modifications in the above-described methods and compositions can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, and all changes which come within the meaning and range of equivalency of the embodiments described herein are therefore intended to be embraced therein.

What is claimed is:

1. An isolated antibody which specifically binds to a peptide or protein comprising an epitope of at least 5 amino acids, said epitope having a GRG motif wherein the arginine is methylated, but does not specifically bind to the peptide or protein when the arginine is not methylated.

2. An isolated antibody generated by immunization of an animal with a synthetic peptide, which antibody specifically binds to a peptide or protein comprising an epitope of SEQ ID NO:1, said epitope having at least one arginine being methylated, but does not specifically bind to the peptide or protein when the at least one arginine in said epitope is not methylated.

3. The antibody of claim 2, wherein the at least one arginine is dimethylated.

4. The antibody of claim 3, wherein the dimethylation is asymmetrical.

5. The antibody of claim 3, wherein the dimethylation is symmetrical.

6. The antibody of claim 2, wherein all the arginines are asymmetrically dimethylated.

7. A method for detecting the presence of arginine methylated proteins or peptides in a sample comprising the steps of:

a) contacting a sample with an antibody of claim 2; and b) detecting the proteins bound to said antibody.

8. The method of claim 7, wherein the antibody is generated against the peptide of SEQ ID NO:1 and wherein all the arginines in SEQ ID NO:1 are methylated.

9. The method of claim 8, wherein all the arginines in SEQ ID NO:1 are asymmetrically methylated.

* * * * *

```
                       SEQUENCE LISTING

<160> NUMBER OF SEQ ID NOS: 1

<210> SEQ ID NO 1
<211> LENGTH: 16
<212> TYPE: PRT
<213> ORGANISM: artificial sequence
<220> FEATURE:
<223> OTHER INFORMATION: synthetic control peptide

<400> SEQUENCE: 1

Cys Gly Arg Gly Arg Gly Arg Gly Arg Gly Arg Gly
                  5                   10

Arg Gly Arg Gly
             15
```